United States Patent [19]

Smyth et al.

[11] 4,170,823

[45] Oct. 16, 1979

[54] FLUORESCENT ARTIFICIAL TEETH

[75] Inventors: Milagros B. Smyth, East Brunswick; James Lee-You, Cranbury, both of N.J.

[73] Assignee: Johnson & Johnson, New Brunswick, N.J.

[21] Appl. No.: 877,588

[22] Filed: Feb. 13, 1978

Related U.S. Application Data

[63] Continuation-in-part of Ser. No. 763,450, Jan. 27, 1977, abandoned.

[51] Int. Cl.$^2$ .............................................. A61C 13/00
[52] U.S. Cl. .............................................. 32/8; 32/2; 250/461 R; 252/301.4 F; 252/301.4 R
[58] Field of Search ...................... 250/461 R; 32/2, 8; 252/301.4 R, 301.4 F

[56] References Cited

U.S. PATENT DOCUMENTS

| | | | |
|---|---|---|---|
| 2,000,285 | 5/1935 | Hoffman | 106/6 |
| 2,301,174 | 11/1942 | Dietz | 250/461 R |
| 2,377,382 | 6/1945 | Slack, Jr. | 32/8 |
| 2,895,050 | 7/1959 | Lee | 250/461 R |
| 3,069,773 | 12/1962 | Saffir | 32/8 |
| 3,400,097 | 9/1968 | Weinstein et al. | 32/8 |
| 3,981,819 | 9/1976 | Yocom et al. | 252/301.4 F |
| 4,014,812 | 3/1977 | Kelsey, Jr. et al. | 252/301.4 F |
| 4,052,329 | 10/1977 | Fukuda et al. | 252/301.4 F |

OTHER PUBLICATIONS

*J. Electrochem. Soc.,* vol. 118, No. 6, Jun. 1971, p. 918, K. R. Laud, E. F. Gibbons, T. Y. Tien, and H. L. Stadler, "Cathodoluminescence of $Ce^{3+}$- and $Eu^{2+}$-Activated Earth Feldspars".

*Journal of Luminescence,* vol. 6, 1973, pp. 425–431, J.M.P.J. Verstegens, J. L. Sommerdijk and J. G. Verriet, "Cerium and Terbiam Luminescence in $LaMgAl_{11}O_9$".

*Primary Examiner*—Louis G. Mancene
*Assistant Examiner*—Michael J. Foycik

[57] ABSTRACT

An artificial porcelain tooth product containing a combination of terbium and cerium salts to produce a desired fluorescence.

3 Claims, No Drawings

FLUORESCENT ARTIFICIAL TEETH

This patent application is a continuation-in-part of U.S. patent application Ser. No. 763,450; filed on Jan. 27, 1977 now abandoned in the names of Smyth, Milagros B., et al.

This invention relates to artificial porcelain teeth that fluoresce in ultraviolet light similar to natural teeth.

Natural teeth have a white fluorescence under ultraviolet light. When making artificial teeth of porcelain, generally some type of fluorescing agent is added to try to produce porcelains having a fluorescene close to that of natural teeth. Generally, various uranium compounds are used, in small amounts, in order to produce the desired fluorescence in porcelains. However, there is some concern in using uranium compounds in artificial teeth due to the known undesirable properties of uranium. Hence, it has been desired for some time now, to remove uranium compounds from artificial porcelain while maintaining the fluorescing properties.

In U.S Pat. No. 2,895,050 there is disclosed a combination of uranium oxides and cerium oxides along with certain other rare earth oxides which it is stated produces fluorescence close to that of natural teeth. Over the years rare earths have been known and used in soda lime glasses to produce a visible fluorescence or luminescence in these glasses.

We have discovered a new fluorescent composition especially suitable for use in manufacturing artificial porcelain teeth. Our new composition does not contain uranium or other radioactive materials and when used in porcelain produces a fluorescence under ultraviolet light considerably superior to that produced by the uranium containing materials. Our new fluorescent composition is a combination of cerium and terbium salts which is incorporated in procelain in specific amounts to produce the desired fluorescence. While it is known that a cerium salt produces one of the more broader absorption spectra of the rare earth materials, it is also known that a terbium salt fluoresces in the blue-green regions.

We have discovered that if you incorporate from about 0.05 to 2.5 percent by weight of terbium oxide, (or a terbium salt in an amount sufficient to provide an equivalent weight of terbium) along with 0.01 to 1.0 percent by weight of cerium oxide, or a cerium salt in an amount sufficient to provide an equivalent weight of cerium, and further provided that when the cerium oxide is at least 0.01 percent to 0.04 percent by weight, the terbium oxide is at least 0.1 percent by weight, and when the terbium oxide is from 0.05 to 0.1 percent by weight, the cerium oxide is at least 0.04 percent by weight, in a vitreous porcelain, you unexpectedly obtain a fluorescence considerably superior to the uranium containing compounds and more comparable to that of natural teeth. Preferably, if from about 0.15 to 1.8 percent by weight of terbium oxide along with from about 0.02 to 0.5 cerium oxide, is incorporated in vitreous porcelain (with the above proviso) an artificial tooth is produced having comparable fluorescing properties to those of natural teeth.

While it is known that terbium will fluoresce in the blue to blue-green color regions, it is believed that the 0.05 to 2.5 percent concentration of terbium oxide in vitreous porcelain fluoresces at a somewhat higher wave length and this amount of terbium oxide combined with the absorption spectra for cerium oxide unexpectedly produces the desired fluorescence as described above.

It should be mentioned that the percentages given above are critical in order to produce the desired fluorescence with porcelains.

Our new fluorescing composition may be used with any dental porcelain to produce the desired fluorescence. In adding our new fluorescing composition to a dental porcelain, it may be added in the desired concentration and mixed with the feldspar and quartz and fired to the desired temperature. The resultant porcelain may then be used in the same manner as standard feldspathic porcelains have been used in the past.

In adding our new fluorescing composition to the lower or medium temperature maturing porcelains, the terbium oxide and cerium oxide are added as powders to the raw materials before the fritting process. It should be mentioned that generally when cerium oxide is added to the frit, it causes undue bubbling and foaming of the frit. However, because we use such a small amount of cerium oxide, we have no problem with adding the cerium oxide to the fused mass and there is no undue bubbling or foaming of the frit.

As previously mentioned the amounts of both rare earth metals used in the vitreous porcelain is extremely important. If less than 0.05 percent terbium is used in the present invention, the desired fluorescence is not provided in the final tooth while using more than 2.5 percent terbium only increases the cost of the final product without improving the fluorescing properties. If less than 0.01 percent cerium is used again the desired fluorescence is not produced in the final product while the use of more than 1 percent cerium will complicate the process for incorporating the cerium with the porcelain without improving the fluorescing properties.

It has also been found that at the lower limits of either cerium oxide and terbium oxide, greater amounts of the other must be incorporated to provide an artificial tooth having the desired fluorescing properties. For example, at a terbium oxide level of from 0.05 to 0.1 weight percent, at least 0.1 weight percent cerium oxide must be incorporated in the artificial tooth and at a cerium oxide level of from 0.01 to 0.04 weight percent, at least 0.1 weight percent terbium oxide must be incorporated in the artificial tooth.

Though preferably the amount of terbium oxides used should be between 0.15 to 1.8 percent by weight and the amount of cerium oxide between 0.02 to 0.5 percent by weight, we have found the best ratios from the standpoint of the desired color of fluorescence to be from 0.5 to 1.2 percent by weight of terbium oxide and from about 0.04 to 0.08 percent by weight of cerium oxide. However, from the standpoint of economics along with the desired fluorescing color we prefer to use from 0.15 to 0.5 percent terbium oxide and from 0.1 to 0.5 percent cerium oxide.

Generally, the more terbium incorporated in the porcelain, the less cerium that is required in the porcelain. This is at least true up to the point where about 2 percent terbium is added, over this amount of terbium the amount of cerium should be increased in order to obtain the desired white fluorescence.

The present invention has been described in terms of the oxides of cerium and terbium, however, other salts of both terbium and cerium may be used. For example, the acetate, acetate hydrate, carbonate, citrate, hydroxide, nitrate, oxalate or sulfate of cerium may be used along with the hydroxide, nitrate, sulfate or oxalate of terbium in order to obtain the desired advantages of the present invention. Throughout the instant specification and the claims, the terms terbium oxide and cerium oxide will include these other salts, however, the amount of such other salts must be adjusted to give equivalent amounts of cerium and/or terbium in the artificial tooth.

The following examples more fully describe the present invention.

EXAMPLE I 0.5 gram of terbium oxide ($Tb_2O_3$) and 0.1 gram of cerium oxide ($CeO_2$) are mixed and ground with 100 grams of a vitreous porcelain. The resultant mixture is fritted and chips taken from the frit in the same manner as teeth are molded from a frit. The resultant chip has a blue-white fluorescence.

EXAMPLE II 1 gram of terbium oxide ($Tb_2O_3$) and 0.1 gram of cerium oxide ($CeO_2$) are mixed with 100 grams of a vitreous porcelain. The resultant mixture is fritted and chips taken from the frit in the same manner as teeth are molded from a frit. The resultant chip has a white fluorescence.

EXAMPLE III

The procedures of Examples I and II are followed as described therein except that 2.5 grams of $Tb_2O_3$ is used and 0.1 gram of $CeO_2$ is used. The resultant chip has a yellowish-white fluorescence.

EXAMPLE IV

The procedures of Examples I and II are followed as described therein except that 0.05 grams of $Tb_2O_3$ is used and 0.01 grams of $CeO_2$ is used. The resulting chip has poor fluorescence. However, increasing the $CeO_2$ to 0.04 grams produced a chip having adequate fluorescence.

EXAMPLE V

The procedures of Examples I and II are followed as described therein except that 0.05 grams of $Tb_2O_3$ is used and 0.01 grams of $CeO_2$ is used. The resultant chip has poor fluorescence. However, increasing the $Tb_2O_3$ to 0.1 grams provided a chiping having adequate fluorescence.

Having thus described the invention, what is claimed is:

1. An artificial porcelain tooth product containing from 0.05 percent to 2.5 percent by weight of terbium oxide and from 0.01 percent to 1.0 percent by weight of cerium oxide and provided that when the cerium oxide is from 0.01 percent to 0.04 percent by weight, the terbium oxide is at least 0.1 percent by weight and when the terbium oxide is from 0.05 to 0.1 percent by weight, the cerium oxide is at least 0.04 percent by weight whereby said tooth product has fluorescent properties comparable to those of natural teeth.

2. An artificial tooth in accordance with claim 1 containing from 0.15 to 1.8 percent of terbium oxide and from 0.02 to 0.5 percent of cerium oxide.

3. An artificial tooth according to claim 1 containing from 0.5 to 1.2 percent of terbium oxide and from 0.04 to 0.08 percent of cerium oxide.

* * * * *